United States Patent
Lakhani et al.

(10) Patent No.: US 10,488,350 B2
(45) Date of Patent: Nov. 26, 2019

(54) INSPECTION SYSTEM FOR INSPECTING AN INTERNAL COMPONENT OF A MACHINE

(71) Applicant: ABB Schweiz AG, Baden (CH)

(72) Inventors: Hetal V. Lakhani, Irving, TX (US); Cajetan Pinto, (West) Mumbai (IN); Gregory A. Cole, West Hartford, CT (US); Gregory F. Rossano, Enfrield, CT (US)

(73) Assignee: ABB Schweiz AG, Baden (CH)

( * ) Notice: Subject to any disclaimer, the term of this patent is extended or adjusted under 35 U.S.C. 154(b) by 148 days.

(21) Appl. No.: 15/859,435

(22) Filed: Dec. 30, 2017

(65) Prior Publication Data

US 2018/0188187 A1    Jul. 5, 2018

Related U.S. Application Data (60) Provisional application No. 62/441,224, filed on Dec. 31, 2016.

(51) Int. Cl.
*G01N 21/954* (2006.01)
*G02B 23/24* (2006.01)
(Continued)

(52) U.S. Cl.
CPC ....... *G01N 21/954* (2013.01); *G02B 23/2484* (2013.01); *G06T 7/0004* (2013.01);
(Continued)

(58) Field of Classification Search
CPC ... G01N 2021/9542; G01N 2021/9544; G01N 2021/9546; G01N 2021/9548;
(Continued)

(56) References Cited

U.S. PATENT DOCUMENTS

| 4,139,822 A | 2/1979 | Urich et al. |
| 4,803,563 A | 2/1989 | Dailey et al. |

(Continued)

FOREIGN PATENT DOCUMENTS

WO    2015095543 A1    6/2015

OTHER PUBLICATIONS

Christopher Markman and Ronald J Zawoysky, "Generator In-Situ Inspections a Critical Part of Generator Maintenance Cost Reduction" GE Energy, Mar. 2012, GER-3954C, Schenectady, NY (16 pages).

*Primary Examiner* — Gordon J Stock, Jr.
(74) *Attorney, Agent, or Firm* — Taft Stettinius & Hollister LLP; J. Bruce Schelkopf (57) ABSTRACT

An inspection system for inspecting an internal component of a machine includes a remote controlled vehicle constructed to fit inside a desired portion of the machine; a controller operative to control an operation of the remote controlled vehicle; a tether coupled to the controller and to the remote controlled vehicle, wherein the tether is operative to transmit control signals from the controller to the remote controlled vehicle; and an imaging device extending from a front portion of the remote controlled vehicle and operative to view the internal component. The imaging device has a flexible articulating tip spaced apart from the front portion of the body.

21 Claims, 4 Drawing Sheets

(51) Int. Cl.
*H04N 5/225* (2006.01)
*G06T 7/00* (2017.01)
*G02B 23/26* (2006.01)

(52) U.S. Cl.
CPC ... *H04N 5/2256* (2013.01); *G01N 2021/9546* (2013.01); *G01N 2201/0216* (2013.01); *G01N 2201/0621* (2013.01); *G01N 2201/0853* (2013.01); *G02B 23/2461* (2013.01); *G02B 23/26* (2013.01); *G06T 2207/30164* (2013.01); *H04N 2005/2255* (2013.01)

(58) Field of Classification Search
CPC .......... G01N 21/954; G01N 2201/021; G01N 2201/0216; G01N 2201/0621; G01N 2201/084; G01N 2201/0853; G02B 23/24; G02B 23/2423; G02B 23/2461; G02B 23/2469; G02B 23/2476; G02B 23/2484; G02B 23/2492; G02B 23/26; G06T 2207/30108; G06T 2207/30164; G06T 7/0004; H04N 2005/2255; H04N 5/2256; H04N 5/2257
USPC .......................................... 356/241.1–241.6
See application file for complete search history.

(56) References Cited

U.S. PATENT DOCUMENTS

| | | | |
|---|---|---|---|
| 5,084,764 A * | 1/1992 | Day | G01M 3/005 348/84 |
| 5,423,230 A * | 6/1995 | Olander | H04N 7/185 348/E7.088 |
| 5,650,579 A | 7/1997 | Hatley et al. | |
| 6,100,711 A * | 8/2000 | Hatley | H02K 15/00 324/765.01 |
| 6,672,413 B2 | 1/2004 | Moore et al. | |
| 6,889,783 B1 | 5/2005 | Moore et al. | |
| 7,181,985 B2 * | 2/2007 | MacMillan | F16L 55/30 73/865.8 |
| 7,201,055 B1 | 4/2007 | Bagley et al. | |
| 7,271,894 B2 * | 9/2007 | Devitt | F01D 21/003 356/241.1 |
| 7,520,189 B2 | 4/2009 | Abbasi et al. | |
| 8,378,691 B2 | 2/2013 | Moser et al. | |
| 8,713,999 B2 * | 5/2014 | Hatcher | F01D 21/003 73/112.01 |
| 8,922,640 B2 * | 12/2014 | Hatcher | F01D 21/003 348/159 |
| 9,398,198 B2 * | 7/2016 | Choi | H04N 7/185 |
| 9,703,090 B2 * | 7/2017 | Kell | B23K 26/0096 |
| 9,709,463 B2 * | 7/2017 | DeAscanis | G01M 15/14 |
| 9,759,667 B2 * | 9/2017 | Miasnikov | G01N 21/94 |
| 9,778,141 B2 * | 10/2017 | Bancalari | F01D 21/003 |
| 9,948,835 B2 * | 4/2018 | DeAscanis | H04N 5/2251 |
| 10,041,371 B1 * | 8/2018 | DeAscanis | F01D 21/00 |
| 10,274,718 B2 * | 4/2019 | Letter | G02B 23/2476 |
| 10,281,912 B2 * | 5/2019 | Hollister | G01B 11/25 |
| 2004/0193016 A1 * | 9/2004 | Root | A61B 1/0052 600/146 |
| 2007/0296964 A1 * | 12/2007 | Nishimura | G01N 21/954 356/241.1 |
| 2015/0233787 A1 * | 8/2015 | Eakins | H02K 15/00 73/114.77 |
| 2019/0022849 A1 * | 1/2019 | Akin | B25J 5/005 |
| 2019/0022876 A1 * | 1/2019 | Akin | B25J 19/023 |
| 2019/0022877 A1 * | 1/2019 | Akin | B62D 57/02 |

* cited by examiner

INSPECTION SYSTEM FOR INSPECTING AN INTERNAL COMPONENT OF A MACHINE

TECHNICAL FIELD

The present application generally relates to machine inspection and more particularly, but not exclusively, to an inspection system for inspecting an internal component of a machine.

BACKGROUND

Inspection systems of various types, e.g., for inspecting internal components of machines, remain an area of interest. Some existing systems have various shortcomings, drawbacks and disadvantages relative to certain applications. For example, in some inspection systems, some internal portions of the machine are not observable by the inspection system. Accordingly, there remains a need for further contributions in this area of technology.

SUMMARY

One embodiment of the present invention is unique inspection system for inspecting an internal component of a machine. Another embodiment is a unique inspection system for inspecting an internal component of an electrical machine, the electrical machine having a rotor, a stator and an air gap formed between the rotor and the stator. Other embodiments include apparatuses, systems, devices, hardware, methods, and combinations for inspecting internal components of machines. Further embodiments, forms, features, aspects, benefits, and advantages of the present application shall become apparent from the description and figures provided herewith.

BRIEF DESCRIPTION OF THE FIGURES

The description herein makes reference to the accompanying drawings wherein like reference numerals refer to like parts throughout the several views, and wherein.

DETAILED DESCRIPTION OF THE ILLUSTRATIVE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
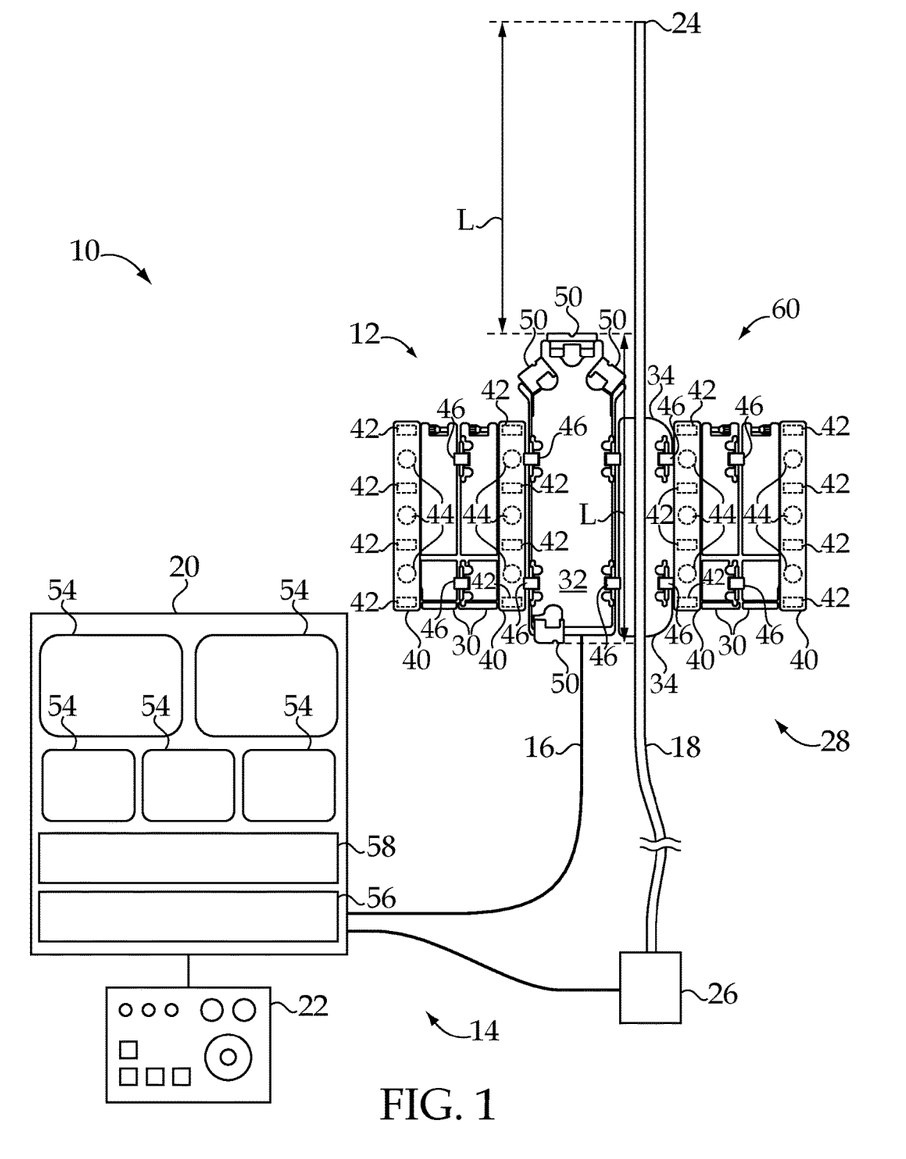
FIG. 1 schematically illustrates some aspects of a non-limiting example of an inspection system in accordance with an embodiment of the present invention.

Referring to FIG. 1, some aspects of a non-limiting example of an inspection system 10 in accordance with an embodiment of the present invention are schematically illustrated. System 10 is constructed to perform inspection of internal components of machines, including electrical machines, e.g., relatively large electrical machines. For example, many types of electrical machines, e.g., long turbo and hydro generators, require service and inspection to maintain a desirable operating condition, e.g., inspection of rotor and stator surfaces, winding overhangs and other internal features, such as cooling ducts, other stator components or features, rotor components or features and other components or features. It is preferable to avoid removing the rotor where possible, as removing the rotor can be a risky and cost prohibitive procedure for some electrical machines, particularly larger electrical machines. In order to perform inspections, it may be possible to utilize a borescope, as the dexterity of the articulable or articulating (capable of articulation or able to be articulated) or steerable tip of the borescope may be useful for visualizing the complex structures within the electrical machine without removing the rotor. In order to inspect with a borescope, it is desirable to guide the borescope tip along a specified path to reach a specified position. For example, while using a flexible borescope, the tip must be guided through the access port and around obstacles to reach the vicinity of a given air duct or stator core or stator core pole or rotor pole or over-hang of the winding.

Some electrical machines have a considerable length, for example, up to 5 meters or more. One of the most important components to inspect is the winding overhang. To manually direct a borescope through an electrical machine from the access port to the other side of the machine up to 5 or more meters away is a difficult task. Considerations for using a borescope to inspect an electrical machine such as a generator include how to control the path traversed by the borescope tip so as to avoid damage to the tip (path control), and how to stop the borescope tip at a fixed distance from a given object, such as the core laminations, to avoid damage, e.g., to the borescope or to the core laminations or other object(s).

For the initial entry, it has been found that the longer the shaft of any stick-like object, e.g., a flexible borescope, the more difficult the task of insertion and control during the inspection process. For flexible borescopes, considerations include that the guidance of the borescope tip along a desired path, e.g., a stator or rotor pole, with lateral restrictions, e.g., stator gaps or teeth, and often in the face of many turning points, is difficult because the display of the images "seen" by the borescope tip may be remote from the control end of the borescope (unless there is direct optical viewing), and there is often a non-intuitive relationship between the control actions employed to manipulate and/or articulate the borescope and the displayed movement.

According, some embodiments of the present invention include systems and methods for using a magnetic air gap crawler to deliver the tip of a borescope to the desired location and holding it there; and an attachment of the borescope to the crawler, which can be expressed as an integrated feature of the crawler, or an attachable module that may be attached to the crawler. The use of a magnetic air gap crawler inside a closed machine to carry the borescope to its intended location helps overcome the difficulties discussed above, for example, by directing the borescope tip along a desired inspection path to inspect features along the path if desired, and to reach the exact location that is desired to be inspected, without the difficulty of controlling the path of a long semi-rigid stick-like object along the length of the electrical machine. The mounting of the borescope on the magnetic crawler allows the flexibility of viewing winding over hangs, spaces beyond the core where the crawler cannot reach, the non-drive end of long machines and other areas without the difficulties of path control of the borescope.

In some embodiments, the borescope extends from the front portion of the crawler, e.g., up to or greater than the length of the crawler, so that borescope tip is substantially spaced apart from the crawler, allowing the borescope tip to be positioned for viewing objects and features that are not viewable from any portion of the crawler itself. Mounting the borescope to the magnetic crawler will extend the inspection coverage of the crawler by allowing it to deliver a vision system beyond where it can crawl on its tracks or treads. This will allow the crawler to inspect the overhangs, end windings, and air vents or ducts and other features by providing a flexible, positionable camera, i.e., camera tip 24, described below, distal to the crawler's vision system. The borescope is attached to the crawler, which give the borescope and tip an effective mechanical ground.

System 10 includes a remote controlled vehicle 12; a controller 14; a tether 16; and an imaging device 18. Controller 14 is operative to control the operation of remote controlled vehicle 12. Tether 16 is coupled to controller 14 and to remote controlled vehicle 12, and is operative to transmit control signals from controller 14 to remote controlled vehicle 12 and supply power to the remote controlled vehicle 12 from controller 14. In addition, tether 16 is operative to transmit image data from remote controlled vehicle to controller 14. Controller 14 includes a control cabinet 20 and an input device 22. Control cabinet 20 is operative to control remote controlled vehicle 12, e.g., based on human input, such as input via input device 22. Input device 22 may include, for example, a joystick and speed control inputs to control the motion of remote controlled vehicle 12, and in some embodiments, switches or other control features for controlling lighting, cameras and/or other features of remote controlled vehicle 12. In one form, imaging device 18 is a flexible video borescope, referred to herein as borescope 18. Borescope 18 has an articulating (e.g., articulable) or steerable imaging or camera tip 24 that includes build-in LED lighting. Camera tip 24 may include a suitable lens, the type of which may vary with the needs of the application, e.g., a fish eye lens. In other embodiments, imaging device 18 may take other forms, e.g., a fiber optic borescope with an articulating or steerable tip having an objective lens and lighting and image capture provided by fiber optic elements, or another form of an articulable camera tip.

Borescope 18 includes a control module 26 operative to control the articulation of tip 24, e.g., via levers or dials (not shown). Borescope 18 is coupled to control cabinet 20 for supplying power to operate camera tip 24 and for processing and display of image data, e.g., video image data or still image data received from camera tip 24, and control of camera tip 24 lighting. In some embodiments, control module 26 may also or alternatively be constructed to control the lighting and operation of camera tip 24, and in some embodiments, to display image data provided by camera tip 24. In one form, camera tip 24 is four-way articulable, i.e., capable of articulating left, right, up and down. In other embodiments, tip 24 may be two-way articulable, e.g., up and down or left and right articulation. In other embodiments, the control module 26 can be integrated with input device 22 to provide a single input device, thereby potentially streamlining operations for the user.

In one form, remote controlled vehicle 12 is a magnetic air gap crawler, and is referred to herein as magnetic air gap crawler 12 or crawler 12. In other embodiments, remote controlled vehicle 12 may take other forms. Crawler 12 is constructed to fit within and move about within a desired portion of a machine being inspected, e.g., an electrical machine being inspected, such as a generator or a motor. For example, crawler 12 is constructed to fit within and move about within the air gap between the stator and the rotor in an electrical machine, e.g., including crawling along the length of the stator core or rotor of the electrical machine. In the illustrated embodiments, crawler 12 includes a body 28 having four (4) drive modules 30, a central module 32 and a borescope module 34. In other embodiments, crawler 12 may take other forms, and may have a greater or lesser number of modules and/or different modules.

Each drive module 30 includes a motor-driven track or tread 40 supported by rollers 42, and provides propulsion to crawler 12. Drive modules 30 are adhered to ferrous or other magnetic materials, such as stator core materials, by magnets 44 disposed adjacent to and under tracks 40. The two outer drive modules 30 are coupled to the two inner drive modules 30 on each side via hinge joints 46. The two inner drive modules 30 are coupled to respective central module 32 and borescope module 34 by hinge joints 46. Borescope module 34 is coupled to central module 32 by a hinge joint 46. Hinge joints 46 allow the various modules of crawler 12 to shift and rotate relative to each other as necessary to operate in confined spaces on curved or compound surfaces, such as the inner surface of an electrical machine stator, e.g., a motor or generator stator, in the air gap between the stator and the rotor.

Central module 32 is coupled to controller 14 via tether 16, and receives power for operating drive modules 30 and camera modules 50 from control cabinet 20 via tether 16. Central module 32 is electrically coupled to each drive module 30 and supplies electrical power for driving each drive module 30 from control cabinet 20. Central module 32 includes a plurality of camera modules 50, each of which includes a camera and a light, e.g., an LED light. Camera modules 50 are operative to capture still image data and video image data of machine components in the vicinity of crawler 12. In addition, central module 32 is operative to transmit image data from camera modules 50 to control cabinet 20 via tether 16. Control cabinet 20 includes a plurality of display monitors 54 for displaying the image data captured by camera modules 50 and borescope 18. Control cabinet 20 also includes a logic and control board 56 with inputs for receiving tether 16 and input device 22, and in some embodiments for receiving image data from borescope 18, e.g., via control module 26. In some embodiments, control cabinet 20 also includes an image recorder 58, such as a digital video recorder, for recording video and still image data from camera modules 50 and borescope 18. In some embodiments, control cabinet 20 includes a keyboard (not shown). In some embodiments, control module 26 also includes a display monitor and may or may not be connected to the control cabinet 20.

Borescope 18 is coupled or affixed to borescope module 34. Borescope module 34 is constructed to carry and support borescope 18. In some embodiments, borescope module 34 is constructed to space borescope 18 from the component the electrical machine that crawler 12 is moving or crawling along, e.g., so that tip 24 does not scrape and drag against the component during motion of crawler 12. Borescope 18 extends from a front portion 60 of body 28 of crawler 12, e.g., is cantilevered off borescope module 34 at front portion 60. In other embodiments, a separate borescope module may not be employed, and borescope 18 may be affixed to and carried by central module 32 or one of drive modules 30. In some embodiments, borescope module 34 is removably attached or coupled to crawler 12, e.g., to central module 32 and the inner right drive module 30. In other embodiments, borescope module 34 may be removably or permanently attached or coupled to any other module or modules, e.g., any one or two modules 30, 32.

Borescope module 34 includes a clasping or clamping mechanism constructed to secure borescope 18 to borescope module 34, e.g., to removably attached borescope 18 to borescope module 34. In one form, clamping screws are employed to secure borescope 18 in place. In other embodiments, other forms of clasping or clamping mechanisms may be employed. In some embodiments, borescope module 34 may have a variable sized or adjustable clasping or clamping mechanism such that more than one diameter and/or type of borescope 18 may be coupled or attached or affixed to the borescope module 34. In some embodiments, borescope 18 may include or employ different types or sizes of removably attachable articulable or articulating tips 24. In other embodiments, the inspection system may include more than one sized borescope module 34 that can support a variety of sizes for borescope 18. In other embodiments, the same borescope 18 could be removed and reattached differently, e.g., in a different position, such that more or less of the length borescope extends in front of crawler 12, as desired by the user or operator. Some embodiments may enable the inspection system, e.g., crawler 12, to carry different borescopes with different capabilities suited to various inspection tasks and conditions. Some embodiments may also or alternatively enable the same borescope to perform different inspection tasks, e.g., by changing the length that the borescope tip extends from the front of the crawler 12. In some embodiments, more than one borescope 18 and borescope module 34 may be employed. In some embodiments, crawler 12 may carry more than one borescope.

In one form, crawler 12 has an overall length L. Camera tip 24 of borescope 18 extends in front of crawler 12 and is disposed in front of and spaced apart from front portion 60. In one form, camera tip 24 is cantilevered off borescope module 34. In some embodiments, camera tip 24 is extends in front of crawler 12 by an amount equal to at least ⅛ of the overall length L of crawler 12. In some embodiments, camera tip 24 extends in front of crawler 12 by an amount equal to at least ⅓ of the overall length L of crawler 12. In some embodiments, camera tip 24 extends in front of crawler 12 by an amount equal to at least the overall length L of crawler 12. The amount of distance that tip 24 extends in front of crawler 12 may vary with the needs of the particular application, and may be, for example, half or ¾ the overall length L of crawler 12, or multiples of the overall length L of crawler 12, e.g., multiples of 1.5, 2, 3, 4 or more, or any suitable value. In some embodiments, the amount of distance that tip 24 extends in front of crawler 12 may be adjustable, so as to meet the needs of the particular machine being inspected.

Figure 2:
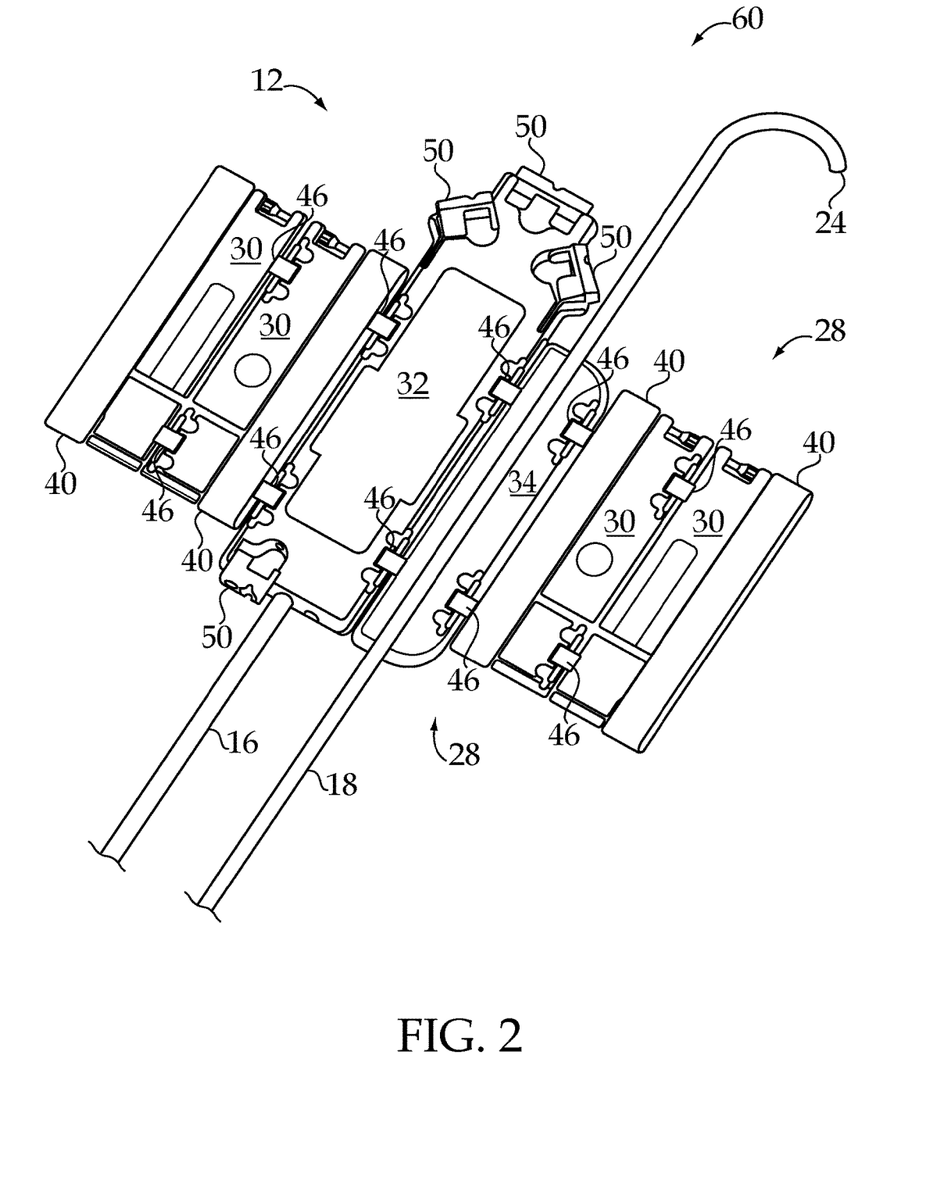
FIG. 2 schematically illustrates some aspects of a non-limiting example of a crawler with an attached borescope in accordance with an embodiment of the present invention.

Referring to FIG. 2, some aspects of a non-limiting example of crawler 12 with borescope 18 in accordance with an embodiment of the present invention are illustrated. In the illustration of FIG. 2, camera tip 24 is articulated in the same plane as borescope module 34 to point in a direction almost facing toward front portion 60 of body 28 of crawler 12. It will be understood that camera tip 24 may be articulated out of the plane of module 34. As is seen in FIG. 2, the locus of articulation of camera tip 24, e.g., the place of articulation or area of articulation or center of articulation of camera tip 24, is spaced apart, e.g., substantially spaced apart, from the front portion 60 of body 28 of crawler 12. For example, the locus of articulation is substantially spaced apart from the front of crawler 12 and/or borescope module 34. The amount of distance that the locus of articulation is spaced apart may vary with the needs of the application, but it may be up to or greater than the length of borescope module 34 or of crawler 12. The amount of distance that the locus of articulation is spaced apart from the front of crawler 12 may vary with the needs with the application, and in some embodiments is variable, i.e., may be adjusted by moving borescope 18 within borescope module 34 fore or aft to a desired location and clamping borescope 18 at the desired location to yield a desired spacing of the locus of articulation apart from the front of module 34 or crawler 12. Camera tip 24 is operative to articulate and view components or features of the electrical machine inside of which crawler 12 is positioned, including components or features that are not line-of-sight observable or otherwise observable by any portion of body 28, including camera modules 50.

By extending and spacing apart camera tip 24 from the body of crawler 12, e.g., from front portion 60 or another portion of crawler 12, and by employing an articulable camera tip 24, e.g., having a locus of articulation spaced apart from the front portion 60 of body 28 of crawler 12, borescope 18 can view features of the electrical machine that are not line-of-sight or otherwise observable from any portion of the body of crawler 12. For example, crawler 12, in the form of a magnetic air gap crawler, is limited to movement upon magnetic surfaces because crawler 12 is adhered to the electrical machine by magnets 44. Because camera tip 24 is spaced apart substantially from the body 28 of crawler 12, e.g., cantilevered off of and extending outward from body 28 a substantial distance, such as from the front-most portion of body 28, camera tip 24 can be delivered by crawler 12 to locations inside the electrical machine that are not reachable by the crawler itself or observable by camera modules 50 mounted on crawler 12 in body 28 or disposed in close proximity to body 28.

Borescope 18, and camera tip 24 in particular, can thus be positioned to capture images of portions of the electrical machine that are not line-of-sight or otherwise observable from the location of any of magnets 44 or any other portion of body 28 of crawler 12, including camera modules 50. Examples of such portions include winding overhangs, cooling vents or ducts and other structures, including both rotor and stator structures. In addition, crawler 12 is operative to guide camera tip 24 along a desired path, e.g., along a particular stator pole or rotor pole, in the process of traveling to those portions of the electrical machine, which is very difficult to do with a borescope manually, i.e., a borescope not mounted on crawler 12. But, with borescope 18 mounted on crawler 12, and with camera tip 24 spaced apart from interior surfaces of the electrical machine a suitable distance, crawler 12 and hence camera tip 24 can be directed via user control to be delivered along the desired path to the desired endpoint, e.g., a winding overhang or cooling duct opening, associated with a particular stator pole that is sought to be investigated by inspection with crawler 12, without dragging or scraping camera tip 24 along the way, and while orienting camera 24 in a desired direction while crawler 12 is traveling. By avoiding any dragging or scraping of camera tip 24 while traveling, damage to surfaces of the machine, e.g., the stator core and rotor, and to camera tip 24 may be avoided. In addition, because the location of camera tip 24 is controlled in part by the position of crawler 12, camera tip 24 can be easily stopped at a fixed distance from any object for the purpose of avoiding damage and/or obtaining a desired image characteristic, e.g., a desired focal distance.

Figure 3A:
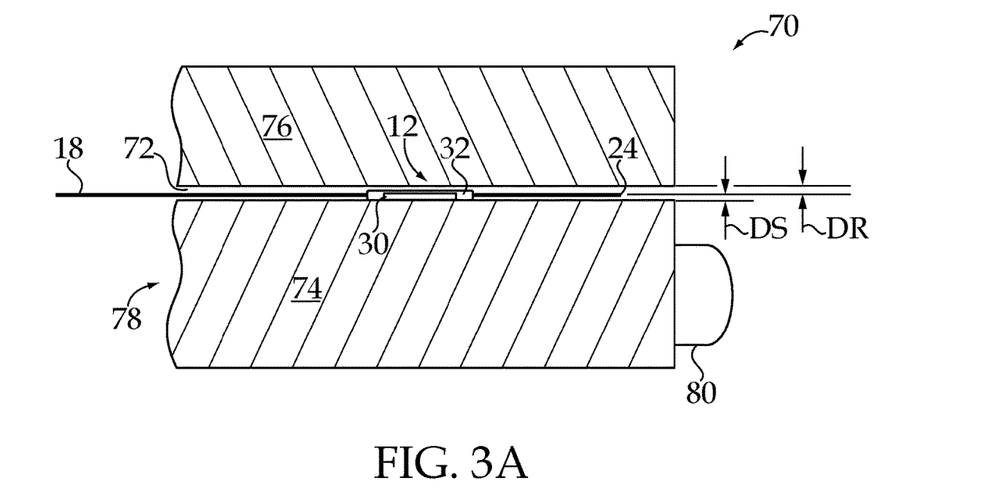
FIGS. 3A-3D schematically illustrates some aspects of a non-limiting example of a crawler with borescope disposed within an air gap inside an electrical machine in accordance with an embodiment of the present invention.

Referring to FIGS. 3A-3D, some aspects of non-limiting examples of crawler 12 carrying or having carried borescope 18 inside an electrical machine 70, e.g., a turbo or hydro generator, are illustrated in accordance with an embodiment of the present invention. In the illustration of FIG. 3A, crawler 12 is disposed inside electrical machine 70 within an air gap 72 between a stator 74 and a rotor 76 of electrical machine 70. Crawler 12 is magnetically adhered to stator 74 by magnets 44, and is able to move along a desired path on stator 74 using tracks 40 of drive modules 30. The desired path may be, for example, a particular stator pole sought to be inspected. Crawler 12 is operative to deliver camera tip 24 along the desired path, while spacing it apart from adjacent structures, such as stator 74 and rotor 76 so that camera tip 24 does not scrape or drag against any surfaces of stator 74 and/or rotor 76, which otherwise may damage camera tip 24 and/or the surfaces of stator 74 and/or rotor 76. In the depiction of FIG. 3A, camera tip 24 is spaced apart from stator 74 a distance DS, and is spaced apart from rotor 76 a distance DR. The orientation of borescope 18 and camera tip 24 may be may be set up to achieve spacing distances DS and DR, e.g., by manually displacing flexible borescope 18, prior to inserting crawler 12 and borescope 18 into air gap 72.

Figure 3B:
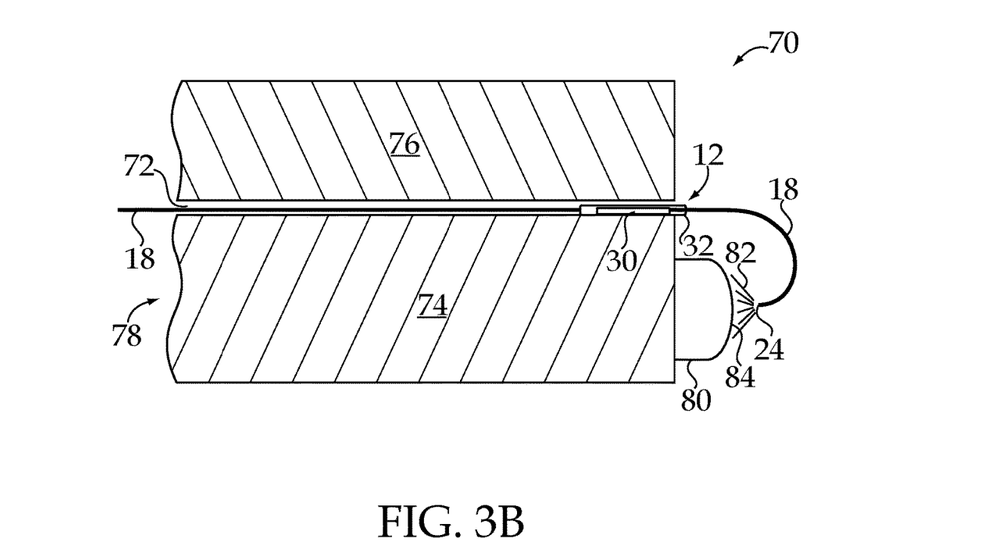

The illustration of FIG. 3B represents a time after the view of FIG. 3A in which crawler 12 had traveled along the desired path, e.g., a stator slot of pole 78 sought to be inspected, e.g., to inspect stator laminations and/or windings, and to reach a desired winding overhang 80 associated with stator pole 78. Lines of view 82 illustrate the camera tip 24 line-of-sight observable portion 84 of winding overhang 80, which are not line-of-sight or otherwise observable to body 28 or any other portion of crawler 12, including camera modules 50. It is seen that forward motion (left to right in the depiction of FIGS. 3A-3D) is limited by the extent of stator 74, since crawler 12 is adhered to stator 74 via magnets 44 disposed adjacent to tracks 40, and that absent the spaced apart and articulable camera tip 24, system 10 would not be otherwise able to view portion 84 of winding overhang 80. However, because camera tip 24 is articulable, e.g., into its illustrated position, and because camera tip 24 extends substantially from crawler 12 (i.e., camera tip 24 is spaced apart substantially from body 28 of crawler 12), e.g., into its illustrated position, portion 84 of winding 80 is line-of-sight observable to camera tip 24. For example, in some embodiments, camera tip 24 is articulable into a position that faces partially toward crawler 12 (e.g., FIGS. 3B, 3C and 3D), and extends sufficiently far in front of crawler 12 that portions of components of electrical machine 70 are disposed at least partially between crawler 12 and camera tip 24, rendering such portions line-of-sight observable to camera tip 24, but not observable by any of the camera modules 50. In some embodiments, camera tip 24 is also articulable into a position that faces wholly or predominantly away crawler 12 and extends sufficiently far in front of crawler 12 and around obstacles inside electrical machine 70 that are not surmountable by crawler 12, such that portions of components of electrical machine 70 are rendered line-of-sight observable to camera tip 24, but not observable to body 28 of crawler 12 or any of the camera modules 50. In various applications, camera tip 24 may be "threaded into" or "snaked into" other locations or passages or openings that thus become line-of-sight observable to camera tip 24, but not line-of-sight or otherwise observable to body 28 of crawler 12 or any of the camera modules 50. Image data from portion 84 captured by camera tip 24 may be sent back to control cabinet 20 via tether 16 for viewing, and in some embodiments also or alternatively for storage and later viewing. In some embodiments, the output of camera tip 24 may also or alternatively be viewable on a separate display, e.g., borescope 18 control module 26. It will be understood that the illustration of FIG. 3B is by way of example only, and that in practice, embodiments of the present invention allow viewing of any structure, component or feature internal to electrical machine 70 that is reachable for line-of-sight viewing by camera tip 24, but not otherwise observable by any other portion of crawler 12, e.g., body 28 or camera modules 50.

Figure 3C:
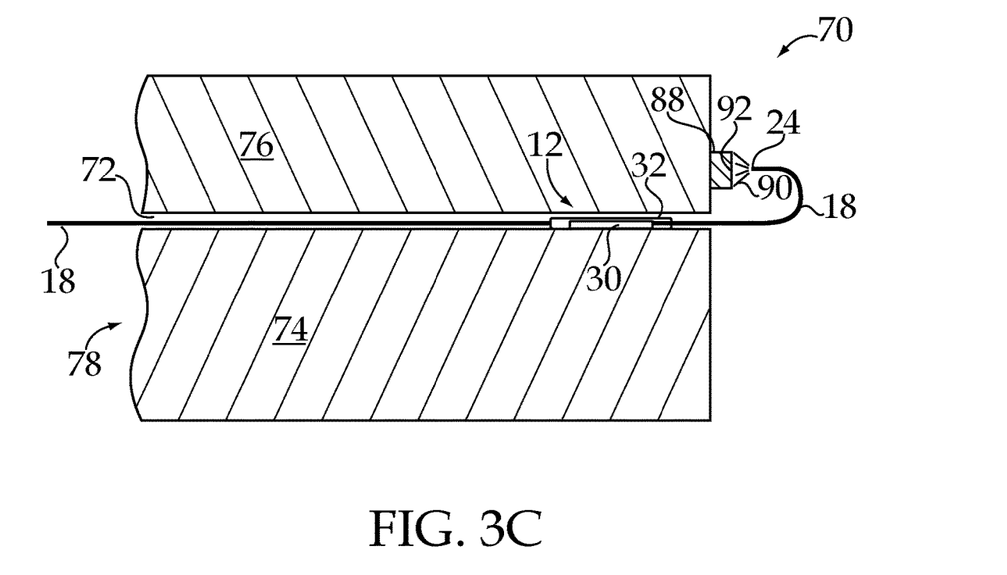

FIG. 3C is similar to FIG. 3B, except that crawler 12 and camera tip 24 are positioned to view a structure 88 on rotor 76. Structure 88 may be any rotor structure, such as a magnetic and/or electrical conductor, or a bearing, a seal or any structure, feature or component internal to electrical machine 70. Lines of view 90 illustrate the camera tip 24 line-of-sight observable portion 92 of structure 88, which are not line-of-sight or otherwise observable to body 28 or any other portion of crawler 12, including camera modules 50. It is seen that forward motion (left to right in the depiction of FIGS. 3A-3D) is limited by the extent of stator 74, since crawler 12 is adhered to stator 74 via magnets 44 disposed adjacent to tracks 40, and that absent the spaced apart and articulable camera tip 24, system 10 would not be otherwise able to view portion 92 of structure 88. However, because camera tip 24 is articulable, e.g., into its illustrated position, and because camera tip 24 extends substantially from crawler 12 (i.e., camera tip 24 is spaced apart substantially from body 28 of crawler 12), e.g., into its illustrated position, portion 92 of structure 88 is line-of-sight observable to camera tip 24. Image data from portion 92 captured by camera tip 24 may be sent back to control cabinet 20 via tether 16 for viewing, and in some embodiments also or alternatively for storage and later viewing. In some embodiments, the output of camera tip 24 may also or alternatively be viewable on a separate display, e.g., borescope 18 control module 26. It will be understood that the illustration of FIG. 3C is by way of example only, and that in practice, embodiments of the present invention allow viewing of any structure, component or feature internal to electrical machine 70 that is reachable for line-of-sight viewing by camera tip 24, but not otherwise observable by any other portion of crawler 12, e.g., body 28 or camera modules 50.

Figure 3D:
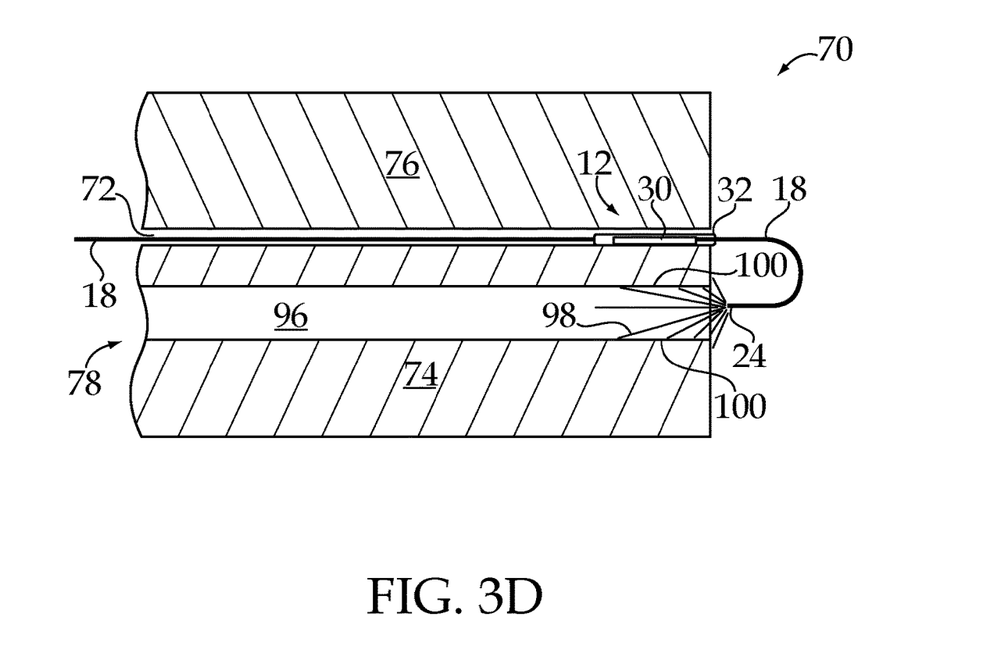

FIG. 3D is similar to FIGS. 3B and 3C, except that crawler 12 and camera tip 24 are positioned to view a passage 96 disposed within stator 74, e.g., a cooling vent or duct. Lines of view 98 illustrate the camera tip 24 line-of-sight observable portion 100 of passage 96, which are not line-of-sight observable to body 28 or any other portion of crawler 12, including camera modules 50. Lines of view 98 illustrate that camera tip 24 can view the area of stator 74 around the entrance to passage 96, as well as the inside of passage 96. It is seen that forward motion (left to right in the depiction of FIGS. 3A-3D) is limited by the extent of stator 74, since crawler 12 is adhered to stator 74 via magnets 44 disposed adjacent to tracks 40, and that absent the spaced apart and articulable camera tip 24, system 10 would not be otherwise able to view portions 100 of passage 96. However, because camera tip 24 is articulable, e.g., into its illustrated position, and because camera tip 24 extends substantially from crawler 12 (i.e., camera tip 24 is spaced apart substantially from body 28 of crawler 12), e.g., into its illustrated position, portions 100 of passage 96 are line-of-sight observable to camera tip 24. Image data from portions 100 of passage 96 captured by camera tip 24 may be sent back to control cabinet 20 via tether 16 for viewing, and in some embodiments also or alternatively for storage and later viewing. In some embodiments, the output of camera tip 24 may also or alternatively be viewable on a separate display, e.g., borescope 18 control module 26. It will be understood that the illustration of FIG. 3D is by way of example only, and that in practice, embodiments of the present invention allow viewing of any structure, component or feature internal to electrical machine 70 that is reachable for line-of-sight viewing by camera tip 24, but not otherwise observable by any other portion of crawler 12, e.g., body 28 or camera modules 50.

Embodiments of the present invention include an inspection system for inspecting an internal component of a machine, comprising: a remote controlled vehicle constructed to fit inside a desired portion of the machine, the remote controlled vehicle having a body with a front portion; a controller operative to control an operation of the remote controlled vehicle; a tether coupled to the controller and to the remote controlled vehicle, wherein the tether is operative to transmit control signals from the controller to the remote controlled vehicle; and an imaging device extending from the front portion of the body of the remote controlled vehicle and operative to view the internal component, the imaging device having a flexible articulating tip spaced apart from the from the front portion of the body.

In a refinement, the articulating tip is positionable to capture images of portions of the internal component that are not line-of-sight observable from any portion of the body of the remote controlled vehicle when the remote controlled vehicle is disposed within the desired portion of the machine.

In another refinement, the articulating tip has a locus of articulation disposed in front of and spaced apart from the front portion of the remote controlled vehicle.

In yet still another refinement, the body has an overall length, and the articulating tip extends in front of the remote controlled vehicle by at least an amount equal to the overall length of the body.

In a further refinement, the imaging device is a flexible borescope.

In a yet further refinement, the remote controlled vehicle is a magnetic air gap crawler.

In a still further refinement, the magnetic air gap crawler includes a plurality of magnets operative to adhere the magnetic air gap crawler to the machine; and the imaging device is positioned to capture images of a portion of the internal component that is not line-of-sight observable from a location of any magnets of the plurality of magnets.

Embodiments of the present invention include an inspection system for inspecting an internal component of an electrical machine, the electrical machine having a rotor, a stator and an air gap formed between the rotor and the stator, comprising: a remote controlled vehicle constructed to fit within the air gap, the remote controlled vehicle having a body, and the remote controlled vehicle being operative to transport itself along the stator and/or the rotor inside the air gap; a controller operative to control an operation of the remote controlled vehicle; a tether coupled to the controller and to the remote controlled vehicle, wherein the tether is operative to transmit control signals from the controller to the remote controlled vehicle; and an imaging device having an articulable tip extending from the body of the remote controlled vehicle wherein the articulating tip has a locus of articulation disposed in front of and spaced apart from the front portion of the remote controlled vehicle.

In a refinement, the articulating tip is positionable to capture images of portions of the internal component outside the air gap that are not line-of-sight observable from any portion of the body of the remote controlled vehicle when the remote controlled vehicle is disposed within the air gap.

In another refinement, the articulating tip is disposed in front of and spaced apart from the body of the remote controlled vehicle.

In yet still another refinement, the remote controlled vehicle has an overall length, and the tip extends in front of the remote controlled vehicle by at least an amount equal to the overall length.

In a further refinement, the imaging device is a flexible borescope.

In a yet further refinement, the remote controlled vehicle is a magnetic air gap crawler.

In a still further refinement, the magnetic air gap crawler includes a plurality of magnets operative to adhere the magnetic air gap crawler to the stator and/or the rotor; and the imaging device is positioned to capture images of a portion of the internal component that is not line-of-sight observable from a location of any magnets of the plurality of magnets.

In a yet still further refinement, the imaging device is removably attached to the remote controlled vehicle.

In another further refinement, the remote controlled vehicle includes an adjustable clamping mechanism operative to removably attach one or more different sizes of the imaging device to a portion of the remote controlled vehicle.

In yet another refinement, the remote controlled vehicle includes a clamping mechanism operative to removably attach the imaging device to a portion of the remote controlled vehicle, wherein the articulating tip is repositionable by use of the clamping mechanism to be extended to a desired length from a front of the remote controlled vehicle.

In still another further refinement, the remote controlled vehicle includes a removable module constructed to carry the imaging device.

In yet still another further refinement, the locus of articulation is repositionable.

Embodiments of the present invention include an inspection system for inspecting an internal component of an electrical machine, the electrical machine having a rotor, a stator, an air gap formed between the rotor and the stator, comprising: a remote controlled vehicle constructed to fit within the air gap, the remote controlled vehicle having a body and a front portion, and the remote controlled vehicle being operative to transport itself along the stator and/or the rotor inside the air gap; a controller operative to control an operation of the remote controlled vehicle; a tether coupled to the controller and to the remote controlled vehicle, wherein the tether is operative to transmit control signals from the controller to the remote controlled vehicle; and means for obtaining images of a portion of the internal component that is not line-of-sight observable to the body of the remote controlled vehicle when the remote controlled vehicle is disposed in the air gap, wherein the wherein the means for obtaining images has a locus of articulation disposed in front of and spaced apart from the front portion of the remote controlled vehicle.

In a refinement, the means for obtaining images includes a flexible borescope.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

What is claimed is:

1. An inspection system for inspecting an internal component of a machine, comprising:
    a remote controlled vehicle constructed to fit inside a desired portion of the machine, the remote controlled vehicle having a body with a front portion;
    a controller operative to control an operation of the remote controlled vehicle;
    a tether coupled to the controller and to the remote controlled vehicle, wherein the tether is operative to transmit control signals from the controller to the remote controlled vehicle; and
    an imaging device extending from the front portion of the body of the remote controlled vehicle and operative to view the internal component, the imaging device having a flexible articulating tip spaced apart from the front portion of the body.

2. The inspection system of claim 1, wherein the articulating tip is positionable to capture images of portions of the internal component that are not line-of-sight observable from any portion of the body of the remote controlled vehicle when the remote controlled vehicle is disposed within the desired portion of the machine.

3. The inspection system of claim 1, wherein the articulating tip has a locus of articulation disposed in front of and spaced apart from the front portion of the remote controlled vehicle.

4. The inspection system of claim 1, wherein the body has an overall length, and wherein the articulating tip extends in front of the remote controlled vehicle by at least an amount equal to the overall length of the body.

5. The inspection system of claim 1, wherein the imaging device is a flexible borescope.

6. The inspection system of claim 1, wherein the remote controlled vehicle is a magnetic air gap crawler.

7. The inspection system of claim 6, wherein the magnetic air gap crawler includes a plurality of magnets operative to adhere the magnetic air gap crawler to the machine; and wherein the imaging device is positioned to capture images of a portion of the internal component that is not line-of-sight observable from a location of any magnets of the plurality of magnets.

8. An inspection system for inspecting an internal component of an electrical machine, the electrical machine having a rotor, a stator and an air gap formed between the rotor and the stator, comprising:
    a remote controlled vehicle constructed to fit within the air gap, the remote controlled vehicle having a body, and the remote controlled vehicle being operative to transport itself along the stator and/or the rotor inside the air gap;
    a controller operative to control an operation of the remote controlled vehicle;
    a tether coupled to the controller and to the remote controlled vehicle, wherein the tether is operative to transmit control signals from the controller to the remote controlled vehicle; and
    an imaging device having an articulating tip extending from and spaced apart from the body of the remote controlled vehicle, wherein the articulating tip has a locus of articulation disposed in front of and spaced apart from the front portion of the remote controlled vehicle.

9. The inspection system of claim 8, wherein the articulating tip is positionable to capture images of portions of the internal component outside the air gap that are not line-of-sight observable from any portion of the body of the remote controlled vehicle when the remote controlled vehicle is disposed within the air gap.

10. The inspection system of claim 8, wherein the articulating tip is disposed in front of and spaced apart from the body of the remote controlled vehicle.

11. The inspection system of claim 8, wherein the remote controlled vehicle has an overall length, and wherein the articulating tip extends in front of the remote controlled vehicle by at least an amount equal to the overall length.

12. The inspection system of claim 8, wherein the imaging device is a flexible borescope.

13. The inspection system of claim 8, wherein the remote controlled vehicle is a magnetic air gap crawler.

14. The inspection system of claim 13, wherein the magnetic air gap crawler includes a plurality of magnets operative to adhere the magnetic air gap crawler to the stator and/or the rotor; and wherein the imaging device is positioned to capture images of a portion of the internal component that is not line-of-sight observable from a location of any magnets of the plurality of magnets.

15. The inspection system of claim 8, wherein the imaging device is removably attached to the remote controlled vehicle.

16. The inspection system of claim 8, wherein the remote controlled vehicle includes an adjustable clamping mechanism operative to removably attach one or more different sizes of the imaging device to a portion of the remote controlled vehicle.

17. The inspection system of claim 8, wherein the remote controlled vehicle includes a clamping mechanism operative to removably attach the imaging device to a portion of the remote controlled vehicle, and wherein the articulating tip is repositionable by use of the clamping mechanism to be extended to a desired length from the front portion of the remote controlled vehicle.

18. The inspection system of claim 8, wherein the remote controlled vehicle includes a removable module constructed to carry the imaging device.

19. The inspection system of claim 8, wherein the locus of articulation is repositionable.

20. An inspection system for inspecting an internal component of an electrical machine, the electrical machine having a rotor, a stator, an air gap formed between the rotor and the stator, comprising:
- a remote controlled vehicle constructed to fit within the air gap, the remote controlled vehicle having a body and a front portion, and the remote controlled vehicle being operative to transport itself along the stator and/or the rotor inside the air gap;
- a controller operative to control an operation of the remote controlled vehicle;
- a tether coupled to the controller and to the remote controlled vehicle, wherein the tether is operative to transmit control signals from the controller to the remote controlled vehicle; and
- means for obtaining images of a portion of the internal component that is not line-of-sight observable to the body of the remote controlled vehicle when the remote controlled vehicle is disposed in the air gap, wherein the wherein the means for obtaining images has a locus of articulation disposed in front of and spaced apart from the front portion of the remote controlled vehicle.

21. The inspection system of claim 19, wherein the means for obtaining images includes a flexible borescope.

\* \* \* \* \*